(12) United States Patent
Sun

(10) Patent No.: US 11,911,744 B2
(45) Date of Patent: Feb. 27, 2024

(54) SUPERABSORBENT MATERIALS AND METHODS OF MAKING THE SAME

(71) Applicant: SIMEON INVESTMENT, INC., Arcadia, CA (US)

(72) Inventor: Lijun Sun, La Canada Fintridge, CA (US)

(*) Notice: Subject to any disclaimer, the term of this patent is extended or adjusted under 35 U.S.C. 154(b) by 53 days.

(21) Appl. No.: 17/339,416

(22) Filed: Jun. 4, 2021

(65) Prior Publication Data

US 2021/0291144 A1   Sep. 23, 2021

Related U.S. Application Data

(60) Division of application No. 16/807,004, filed on Mar. 2, 2020, now Pat. No. 11,045,786, which is a continuation of application No. PCT/US2019/046077, filed on Aug. 10, 2019.

(60) Provisional application No. 62/717,644, filed on Aug. 10, 2018.

(51) Int. Cl.
| | | |
|---|---|---|
| *B01J 20/24* | (2006.01) | |
| *A61K 31/736* | (2006.01) | |
| *B01J 20/30* | (2006.01) | |

(52) U.S. Cl.
CPC .............. *B01J 20/24* (2013.01); *A61K 31/736* (2013.01); *B01J 20/3021* (2013.01); *B01J 20/3078* (2013.01)

(58) Field of Classification Search
CPC .. A61K 31/731; A61K 31/729; A61K 31/734; A61P 3/04; A61P 3/06
See application file for complete search history.

(56) References Cited

U.S. PATENT DOCUMENTS

| | | | |
|---|---|---|---|
| 6,271,278 B1 | 8/2001 | Park et al. | |
| 2003/0224022 A1* | 12/2003 | Nussinovitch | A23P 30/32 435/252.1 |
| 2006/0093720 A1 | 5/2006 | Tatz | |
| 2015/0125568 A1 | 5/2015 | James | |
| 2015/0282510 A1 | 10/2015 | Makita et al. | |
| 2015/0366989 A1 | 12/2015 | Liang et al. | |
| 2017/0319616 A1 | 11/2017 | Lim et al. | |

OTHER PUBLICATIONS

USPTO; International Search Report and Written Opinion issued in Application No. PCT/US19/46077; dated Nov. 13, 2019; 10 pages.
Ni, et al.; "The Control of Ice Crystal Growth and Effect on Porous Structure of Konjac Glucomannan-Based Aerogels"; International Journal of Biologial Macromolecules; 2016; vol. 92; pp. 1130-1135.
Takei, et al.; "Autoclavable physically-crosslinked chitosan cryogel as a wound dressing"; Journal of Bioscience and Bioengineering; 2017; vol. 125; No. 4; pp. 490-495.

* cited by examiner

*Primary Examiner* — Pancham Bakshi

(57) ABSTRACT

Provided are superabsorbent materials composed of agar, and one or more water-soluble natural polysaccharides, and dietary compositions containing such superabsorbent materials. The disclosed superabsorbent materials have various food and therapeutic applications and can be used as loading vehicles for nutrients and therapeutic agents. Also provided are methods for preparing such superabsorbent materials.

21 Claims, 13 Drawing Sheets

| Sample No. | Dry | Rehydration (24 hours) |
|---|---|---|
| 22 |  |  |
| 23 |  |  |
| 24 |  |  |

| Sample No. | Dry | Rehydration (24 hours) |
|---|---|---|
| 25 |  |  |
| 26 |  |  |
| 27 |  |  |

| Sample No. | Dry | Rehydration (24 hours) |
|---|---|---|
| 28 |  |  |
| 29 |  |  |
| 30 |  |  |

| Sample No. | Dry | Rehydration (24 hours) |
|---|---|---|
| 31 |  |  |
| 32 |  |  |

Sample No. 22

Sample No. 23

Sample No. 24

Sample No. 27

| Sample No. | Perspective A | Perspective B |
|---|---|---|
| 22 |  |  |
| 23 |  |  |
| 24 |  |  |

| Sample No. | Perspective A | Perspective B |
|---|---|---|
| 25 |  |  |
| 26 |  |  |
| 27 |  |  |
| 28 |  |  |

| Sample No. | Perspective A | Perspective B |
|---|---|---|
| 29 |  |  |
| 30 |  |  |
| 31 |  |  |
| 32 |  |  |

| Sample No. | Perspective A | Perspective B |
|---|---|---|
| 22 |  |  |
| 23 |  |  |
| 24 |  |  |
| 25 |  |  |

| Sample No. | Perspective A | Perspective B |
|---|---|---|
| 26 |  |  |
| 27 |  |  |
| 31 |  |  |
| 32 |  |  |

| Sample No. | Perspective A | Perspective B |
|---|---|---|
| 22 |  |  |
| 23 |  |  |
| 24 |  |  |

| Sample No. | Perspective A | Perspective B |
|---|---|---|
| 25 |  |  |
| 26 |  |  |
| 27 |  |  |

SUPERABSORBENT MATERIALS AND METHODS OF MAKING THE SAME

CROSS-REFERENCE TO RELATED APPLICATIONS

This application is a divisional of U.S. application Ser. No. 16/807,004 filed Mar. 2, 2020, which is a continuation of International Patent Application No. PCT/US2019/046077 filed Aug. 10, 2019, which claims the benefit of U.S. Provisional Patent Application No. 62/717,644 filed Aug. 10, 2018, which applications are incorporated herein by specific reference in their entirety.

TECHNICAL FIELD

This disclosure relates to superabsorbent materials prepared from agar, carrageenan, a mixture of agar and one or more water-soluble natural polysaccharides, or a mixture of carrageenan and one or more water-soluble natural polysaccharides, and methods of making such superabsorbent materials. The superabsorbent materials have various applications in the field of food and health supplement industry or as a delivery vehicle.

BACKGROUND

With the improvement of living standards, the increasing pace of life style, and at the same time reduction of exercise and irregular diet, the obese or overweight population is increasing at an alarming pace. A study recently published by The New England Journal of Medicine projected that 57.3% of today's children will be obese by age 35. Such bleak prediction highlights the devastating health problem of obesity. Obesity is a major social and economic burden worldwide accounting for two trillion dollars per year spent on healthcare of obesity-related diseases. Obesity is the underlying cause of many medical complications, such as diabetes, high blood pressure, high cholesterol and various cardiovascular and cerebrovascular diseases. The health risk of obesity is now well recognized, and as a major means to fight obesity, weight control by healthy diet and exercise has received widespread attention. Extensive research suggests that high-carbohydrate and high-fat diets are the main causes of obesity. When the consumed food contains too many calories, the body takes in more calories than it normally uses, and the excess calories will be stored in the form of fat, thereby leading to obesity. Thus, controlling the amount of food calorie intake is a key strategy in weight control.

There are many different types of weight-loss diet on the market. Among them, one class contains the main functional ingredients that include dietary fiber, sometimes also supplemented with other essential nutrients. These optimized dietary goods are used to replace high-calorie diets to reduce calorie intake and increase satiety. Accordingly, there is a need in the art to develop an improved dietary product comprising natural polysaccharides that can induce satiety when a small amount of the product is consumed.

SUMMARY

In one aspect, provided herein is a superabsorbent material comprising agar, carrageenan, a combination of agar and one or more water-soluble natural polysaccharides, or a combination of carrageenan and one or more water-soluble natural polysaccharides. In some embodiments, the superabsorbent material comprises at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% (wt %) of agar. In some embodiments, the superabsorbent material comprises at least 20% (wt %) of carrageenan. The agar or carrageenan and the one or more water-soluble natural polysaccharides do not form any chemical cross-linkage in the superabsorbent material but rather form strong molecular interactions induced by cryogelation or cryostructuing to result in a highly porous network structure. The porous network structure is highly stable and reversible in the drying and rehydration processes under neutral and low pH solution mimicking human gastric condition. The superabsorbent material has a great swelling capacity at room temperature (for example, at a temperature between 15° C. and 25° C.), or at human body temperature (for example, at a temperature between 35° C. and 41° C.), and under a neutral pH condition or a human gastric pH condition. Upon rehydration, the superabsorbent material can expand in volume rapidly in less than 2 hours, less than 1.5 hours, less than 1 hour, less than 30 minutes or less than 15 minutes (for example, in less than 25 minutes) and maintain a well-defined shape for at least 24 hours, at least 36 hours, or at least 48 hours under a neutral pH condition or a human gastric pH condition. In some embodiments, upon rehydration, the superabsorbent material can expand in volume rapidly in less than 25 minutes and maintain a well-defined shape for at least 24 hours under a neutral pH condition or a human gastric pH condition.

In some embodiments, the swelling capacity of the superabsorbent materials is measured by absorption ratio calculated by the formula: the weight of fully rehydrated sample/the weight of dry sample. For example, the superabsorbent material disclosed herein has an absorption ratio of at least 10 times or up to 200 times of its own weight in deionized water, or at least 5 times or up to 100 times of its own weight in artificial gastric juice. In some embodiments, the volume expansion capacity of the superabsorbent materials is measured by volume expansion ratio calculated by a formula: the volume of fully rehydrated sample/the volume of dry sample. For example, the superabsorbent material disclosed herein has a volume expansion ratio of at least 5 times or up to 150 times in deionized water, or a volume expansion ratio of at least 5 times to up to 100 times in artificial gastric juice. In some embodiments, the one or more water-soluble natural polysaccharides include but are not limited to konjac gum, carrageenan, locust bean gum, xanthan gum, tamarind seed gum and guar gum carrageenan, alginate (such as sodium alginate), pectin, gellan gum, chitosan, Arabic gum, and a soluble starch. The superabsorbent materials can be obtained by the process disclosed herein.

In another aspect, provided herein is a dietary composition comprising the superabsorbent material described above. In another aspect, provided herein is a volumetrics diet comprising the superabsorbent material or the dietary composition disclosed herein.

In another aspect, provided herein is a method of preventing or treating a disease or condition associated with abnormal metabolism. The method comprises orally administering to a subject suffering from or at an elevated risk of a disease or condition associated with abnormal metabolism an effective amount of the superabsorbent material, the dietary composition comprising the superabsorbent material or the volumetrics diet described above. In some embodiments, the disease or condition associated with abnormal metabolism includes but is not limited to diabetes, obesity, overweight, high cholesterol, and high blood pressure.

In another aspect, provided herein is a method of suppressing appetite, enhancing satiety, or lowering calorie intake in a subject. The method comprises orally administering to a subject in need thereof an effective amount of the superabsorbent material, the dietary composition comprising the superabsorbent material or the volumetrics diet described above.

In yet another aspect, provided herein is a method of preparing a superabsorbent material comprising agar, carrageenan, a combination of agar and one or more water-soluble natural polysaccharides, or a combination of carrageenan and one or more water-soluble natural polysaccharides. The method comprises the steps of adding agar, carrageenan, a combination of agar and one or more water-soluble natural polysaccharide, or a combination of carrageenan and one or more water-soluble natural polysaccharides to water to form a mixture, heating the mixture to a temperature of between 80° C. and 100° C. with stirring until the one or more polysaccharides are completely dissolved, allowing the mixture to cool down to between 20° C. and 45° C. to form a gel over a period of 2 to 10 hours, freezing the preformed gel at a temperature below freezing temperature for at least 4 hours, and drying the frozen gel to obtain the superabsorbent material. In some embodiments, the drying step comprises thawing the gel and drying under normal pressure at 50-60° C. ("thawing-dry"). In some embodiments, the drying step comprises directly drying the frozen gel by lyophilization without thawing ("freeze-dry"). In some embodiments, the method further comprises pulverizing the dried gel to obtain the superabsorbent material in a powder form of various mesh sizes. In some embodiments, the one or more water-soluble natural polysaccharides include but are not limited to konjac gum, carrageenan, locust bean gum, xanthan gum, tamarind seed gum and guar gum carrageenan, alginate (such as sodium alginate), pectin, gellan gum, chitosan, Arabic gum, and a soluble starch.

In a related aspect, provided herein is a superabsorbent material produced by the method described above. The superabsorbent material produced by the disclosed method can be used in food or health supplement industry and/or as delivery vehicle for therapeutic agents and/or nutrients.

DETAILED DESCRIPTION

Figure 1:
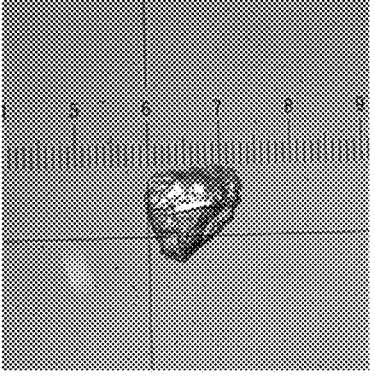
FIG. 1 shows the light microscope images of Sample Nos. 22-32 of the superabsorbent materials before and after rehydration.
Figure 1:
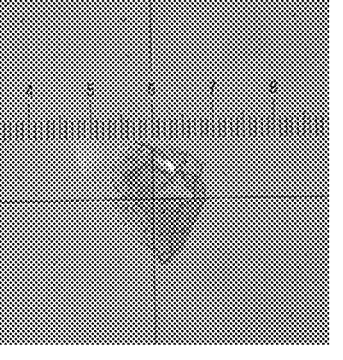
Figure 1:
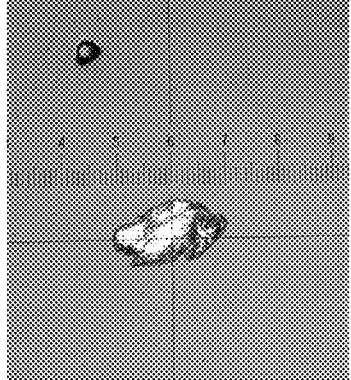
Figure 1:
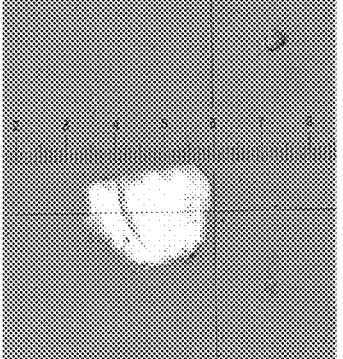
Figure 1:
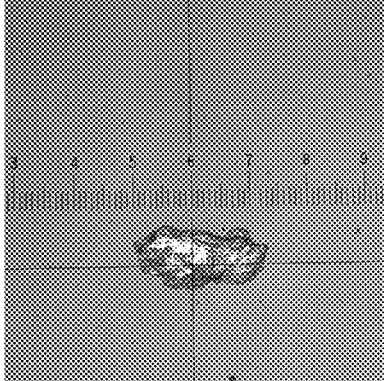
Figure 1:
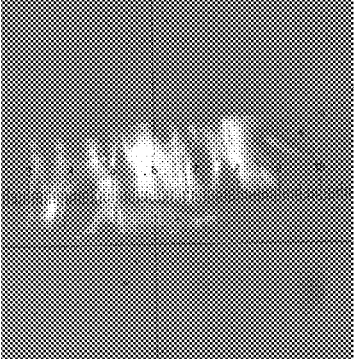
Figure 1:
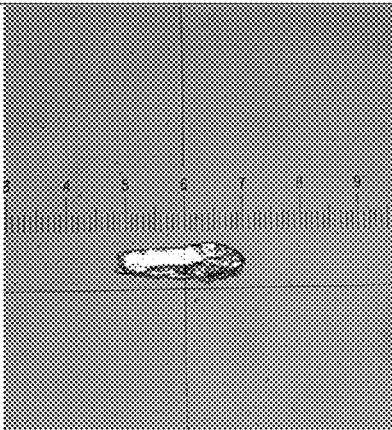
Figure 1:
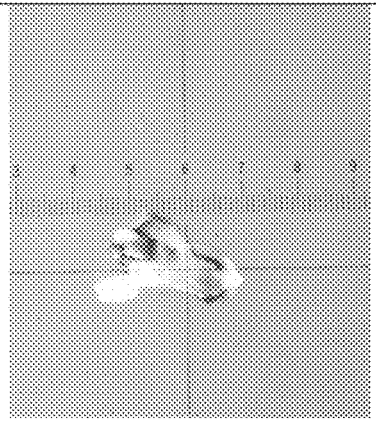
Figure 1:
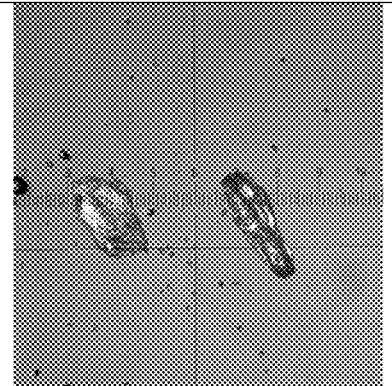
Figure 1:
Figure 1:
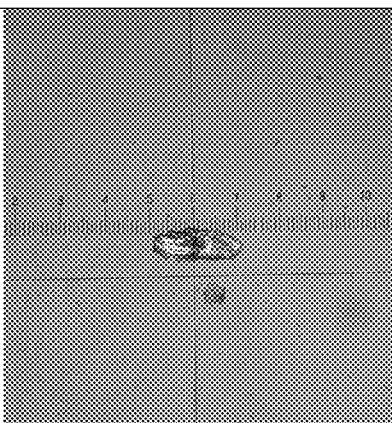
Figure 1:
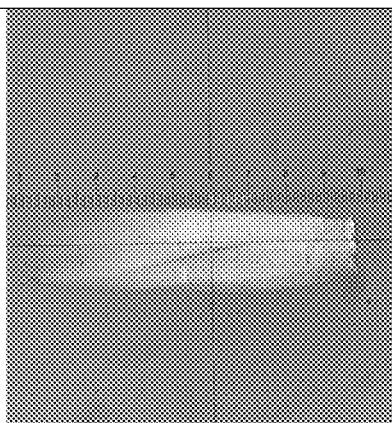
Figure 1:
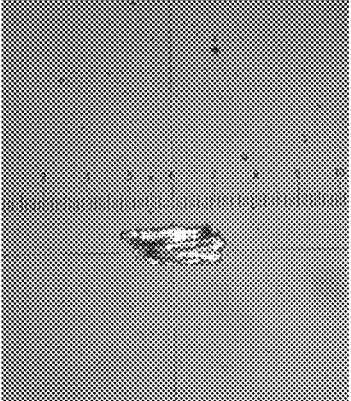
Figure 1:
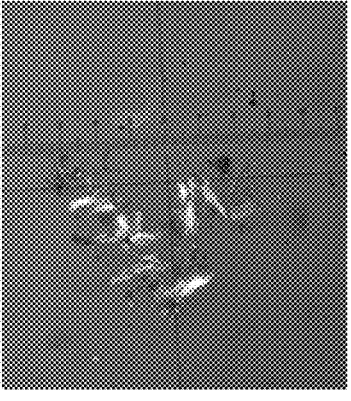
Figure 1:
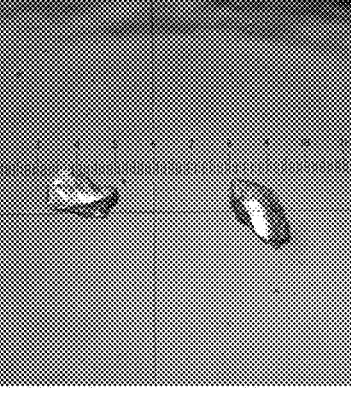
Figure 1:
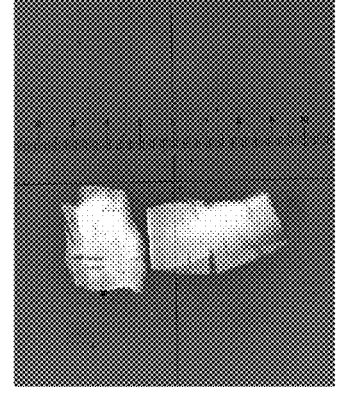
Figure 1:
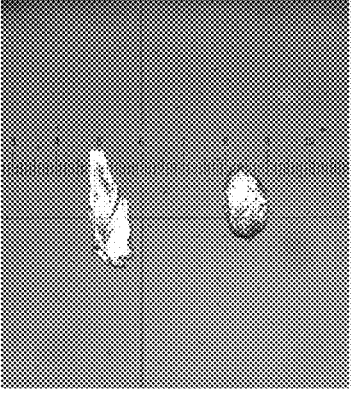
Figure 1:
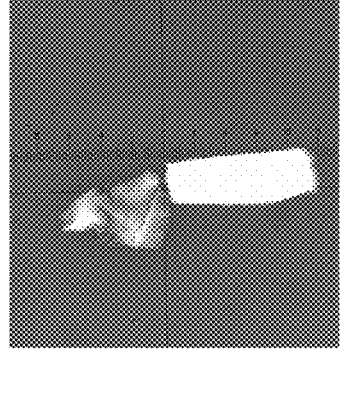
Figure 1:
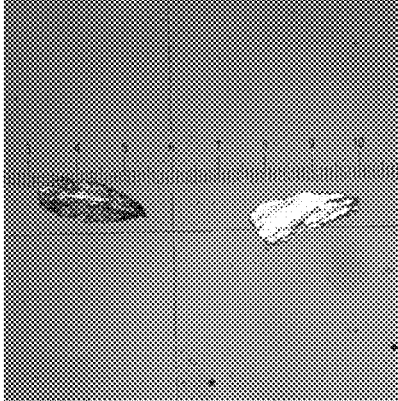
Figure 1:
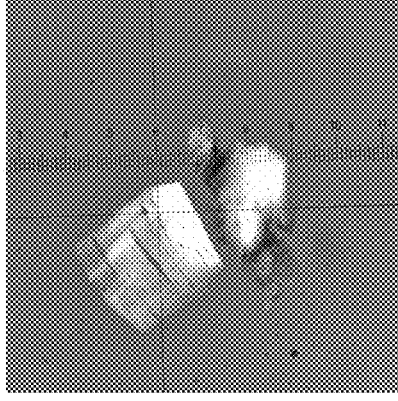
Figure 1:
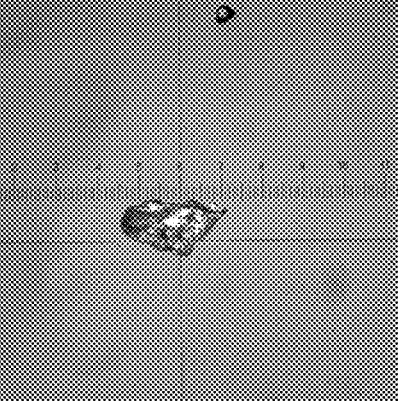
Figure 1:
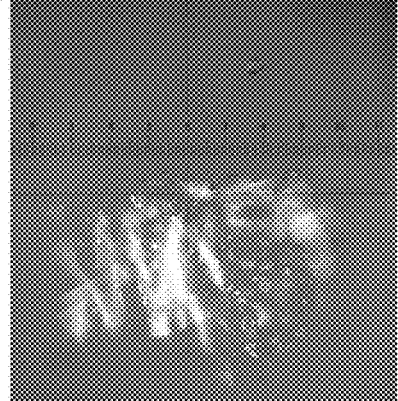

Disclosed herein is a superabsorbent material comprising at least 20% (wt %) agar or carrageenan, and optionally one or more water-soluble natural polysaccharides. In some embodiments, the water-soluble natural polysaccharide includes but is not limited to konjac gum, carrageenan, locust bean gum, xanthan gum, tamarind seed gum and guar gum carrageenan, alginate (such as sodium alginate), pectin, gellan gum, chitosan, Arabic gum, and a soluble starch. The superabsorbent material has a superior swelling capacity (both in terms of water absorption ratio and volume expansion ratio) at room temperature (for example, at a temperature between 15° C. and 25° C.), or at human body temperature (for example, at a temperature between 35° C. and 41° C.), and/or under a neutral pH condition or a human gastric pH condition. In some embodiments, the superabsorbent material disclosed herein have a highly porous structure that is stable and reversible in the drying and rehydration processes under neutral and low pH solution mimicking human gastric condition. Upon rehydration, the superabsorbent material can expand in volume rapidly (in less than 25 minutes) and maintain a well-defined shape for at least 24 hours under a neutral pH condition or a human gastric pH condition. In some embodiments, the superabsorbent material disclosed herein is stable under an acidic pH such as a gastric pH and maintains the structure and the volume under the acidic gastric pH such that the induced satiety effect in a subject is prolonged.

As used herein, the swelling capacity is represented by absorption ratio measured by the following formula: absorption ratio=the wet weight of the superabsorbent material swelled in water or a specific buffer to saturation/the dry weight of the superabsorbent material, and by volume expansion ratio measured by the following formula: volume expansion ratio=the volume of the fully hydrated superabsorbent material soaked in water or a specific buffer to saturation/the volume of the starting dry superabsorbent material. In some embodiments, the absorption ratio and/or the volume expansion ratio is measured at room temperature. In some embodiments, the absorption ratio and/or the volume expansion ratio is measured at about 37° C. In some embodiments, the absorption ratio and/or the volume expansion ratio is measured at a neutral pH. In some embodiments, the absorption ratio and/or the volume expansion ratio is measured at a physiological pH. In some embodiments, the absorption ratio and/or the volume expansion ratio is measured at a gastric pH. In some embodiments, the superabsorbent materials obtained by the process disclosed herein have a water absorption ratio of at least 10 fold, at least 20 fold, at least 30 fold, at least 40 fold, at least 50 fold, at least 60 fold, at least 70 fold, at least 80 fold, at least 90 fold, at least 100 fold, at least 110 fold, at least 120 fold, at least 130 fold, at least 140 fold, at least 150 fold, at least 160 fold, at least 170 fold, at least 180 fold, at least 190 fold, or at least 200 fold of the weight of the dry superabsorbent material before swelling. In some embodiments, the superabsorbent materials obtained by the process disclosed herein have a gastric fluid absorption ratio of at least 5 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, or at least 100 fold of the weight of the dry superabsorbent material before swelling. In some embodiments, the superabsorbent materials obtained by the process disclosed herein have a volume expansion ratio in water of at least 10 fold, at least 20 fold, at least 30 fold, at least 40 fold, at least 50 fold, at least 60 fold, at least 70 fold, at least 80 fold, at least 90 fold, at least 100 fold, at least 110 fold, at least 120 fold, at least 130 fold, at least 140 fold, or at least 150 fold of the weight of the dry superabsorbent material before swelling. In some embodiments, the superabsorbent materials obtained by the process disclosed herein have a volume expansion ratio in gastric fluid of at least 5 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, or at least 100 fold of the weight of the dry superabsorbent material before swelling.

A variety of water-soluble natural polysaccharides including agar, konjac gum, carrageenan, locust bean gum, xanthan gum, tamarind seed gum, guar gum, etc. are known to possess health benefits as dietary fiber with zero calories (undigestible to human enzymes). Attempts to use these dietary fiber materials to control calorie intake, obesity and other health problems have been made by extensive efforts. However, most of the applications involving the use of these natural polysaccharides materials either do not maintain a certain shape upon rehydration with water or gastric liquid or have poor water absorption and volume expanding capability. Therefore, they are cleared by the gastric system quickly and are not very effective in inducing satiety.

Disclosed herein are novel superabsorbent materials that are made from water-soluble natural polysaccharides with known health benefits and/or food application qualities (i.e. gelling strength, desirable texture etc.), so the resulting composite natural polysaccharides have the desirable functionalities including but not limited to quick absorbance of a large amount of water upon rehydration with water or gastric liquid at room temperature (around 25° C.) or body temperature (around 37° C.), and quick swelling in volume and maintaining a certain shape and non-aggregated state in water or gastric liquid. The disclosed superabsorbent materials are effective in inducing satiety and have great applications in weight control and preventing or treating other health problems such as diabetes.

The disclosed superabsorbent materials comprise an optimized combination of natural polysaccharides (composition ratio and total mass concentration). Upon subjecting to a series of physical treatment that induce and/or enhance the interactions between the natural polysaccharide molecules without using any chemical modifications or crosslinking and dehydration, the superabsorbent materials can form and maintain over a prolonged period of time a porous structure. Any dehydration protocol can be used as long as the drying process can maintain the gel matrix structural without diminishing the water absorption capacity and volume expansion function.

To obtain the disclosed superabsorbent materials, a variety of parameters were tested, including various combination of natural polysaccharides (composition ratio and total mass concentration), and various processing methods were carried out to produce a series of composite natural polysaccharides that have a range of water absorption and volume expanding and shape maintaining properties. These natural polysaccharide composite materials with different water absorption, volume expansion and shape stability can be used in a variety of applications. Some examples of the advantages of the disclosed superabsorbent materials and technology are summarized below.

First, synergistic effects in solution and in gelling process of certain natural polysaccharides can be achieved by the selection of the polysaccharides, the particular ratio range of the selected polysaccharides, and the mass concentration range of the materials.

Second, the superabsorbent materials have superior properties in volume expansion and a well-defined shape upon rehydration due to their matrix structure providing enhanced stability and high swelling capacity with respect to absorbent ratio and volume expansion. Unlike conventional technology and materials, the disclosed technology and materials do not use modified or synthetic polymers or chemical crosslinking. As disclosed herein, the gel strength of the materials can be enhanced by freezing treatment of the gel.

Finally, since the final product is in a dehydrated form that can be used to absorb water and expand volume to a certain shape upon rehydration, it is important to develop a process that can remove water from the composite gel while maintaining its structural integrity and functionality. Among the many possible dehydration methods that satisfy the aforementioned criteria, disclosed are a thawing-drying method and a freeze-drying method. By thawing-drying, the preformed gel is thawed and then dried at a temperature (e.g. 50-60° C.) without melting the gel structure under atmospheric pressure. By freeze-drying, the preformed gel is directly lyophilized under vacuum. Both methods yield samples with good to great water absorption and volume expansion properties. In some embodiments, the freeze-dried samples have a more porous structure and higher water absorption capacity, while the thawing-dried samples have a more compact structure in the dry state but can resume a porous structure upon rehydration, although its water absorption capacity is lower than that of freeze-dried samples.

There are a wide range of high-quality water-soluble dietary fibers that are non-toxic to human body, low in calories, and cannot be digested and decomposed by gastric acid and enzymes in the human body. These include seaweed polysaccharides such as agar and carrageenan extracted from marine algae, konjac flour, guar gum, pectin, locust bean gum, tamarind polysaccharide gum, etc. extracted from plants, xanthan gum extracted by microorganism fermentation, microbial polysaccharides such as gellan gum. These natural polysaccharides have the functions of promoting intestinal peristalsis, laxative, detoxification, and preventing intestinal diseases; slowing postprandial blood glucose rise and reducing the risk of diabetes; lowering cholesterol and reducing the risk of cardiovascular and cerebrovascular diseases; and improving the metabolism of neutral fat and lipid and inhibiting body fat accumulation. However, when these natural polysaccharides are directly used in foods, their water absorption and swelling capacity in the stomach is small after consumption, resulting in poor satiety effect. Another problem is that the polysaccharides are quickly dissolved in gastric juice, resulting in a short period of time remaining in the stomach and therefore, the polysaccharides are unable to achieve sustained satiety effect for a prolonged time.

Agar is a water-soluble polysaccharide extracted from red algae. At room temperature, agar can absorb water and swell, but it needs to be heated to above 80° C. to dissolve in water. When the agar solution is cooled to 32-42° C., it will start to solidify into gel, and the solidified agar gel needs to be heated to 75° C. or above before it can melt again. Thus, agar is uniquely advantageous in many applications. In addition, compared with other natural gelling agents, agar has self-gelling property, that is, it does not require any additional substance during gelling process. Thus, agar gel is a purely natural product. Further, agar cannot be digested and absorbed by the human body, and therefore is widely used in food, biological applications and medicine. Carrageenan is another water-soluble polysaccharide extracted from red algae. Based on structural differences, carrageenans are divided into three main classes: Kappa, Iota, and Lambda. K-carrageenan can swell in water at room temperature but can only dissolve in water at a temperature above 70° C. When the carrageenan solution is cooled to 20-25° C., it will start to solidify into gel (or it can form gel at higher temperatures when KCl is added), and the solidified carrageenan gel needs to be heated to 47° C. or above before it can melt again. Konjac gum (konjac glucomannan, KGM) is derived from Amorphophallus Konjac species, it is a high molecular polysaccharide made of residues of mannose and glucose, linked together by β-1,4 with a molar ratio of 1.6:1.0. It is a slightly branched polysaccharide having a molecular weight of 200,000 to 2,000,000 Daltons (actual molecular weight of KGM depends on the konjac variety). As described above, certain types of polysaccharide molecules can interact with each other in solution to generate synergistic effect in gelling process. For example, in a mixed solution of agar that also contains carrageenan and konjac gum, when the temperature is increased to above 80° C., the agar molecules and the carrageenan/konjac gum molecules exist in the form of random coils. As the temperature of the solution decreases, the random coils of agar and possibly some carrageenan/konjac gum molecules start to interact with each other and form double helical structures; when the temperature is further reduced, the double helices will further interact with each other and self-assemble; and when the temperature drops to the gelling point, it can form a three-dimensional porous, network structure composed of agar molecules and carrageenan/konjac gum molecules. When the gel is further frozen for an extended period of time, any polysaccharide molecules, in particular carrageenan/konjac gum molecules, that are not incorporated in the gel matrix in the initial gelling step, may be induced to interact with the preformed agar gel network by the cryogelation effect. As a result, a composite material is formed with a highly stable porous structure that is capable of encapsulating a large amount of water molecules. By removing the water molecules while maintaining the three-dimensional porous, network structure, a superabsorbent material can be obtained.

In general, when a high temperature agar is mixed with one or more water-soluble natural polysaccharides, the agar molecules may interact with the other natural polysaccharide molecules as the temperature of the solution decreases. Due to the different molecular structures of the polysaccharides, the interactions between different natural polysaccharide molecules and the agar molecules are different. The resulting three-dimensional porous network structures and properties of the composite materials made from the agar and one or more water-soluble natural polysaccharide molecules are also different. By removing water molecules while maintaining the three-dimensional porous network structure formed by the agar molecules and the one or more natural polysaccharide molecules, a superabsorbent material can be obtained.

Disclosed herein is a process of obtaining a superabsorbent material comprising the steps of combining agar and one or more water-soluble natural polysaccharides at various ratio and mass concentrations, heating the mixture in water to completely dissolve the agar and one or more water-soluble natural polysaccharides, and forming a gel by cooling the mixture, and further stabilizing the gel by cryogelation below freezing point. The obtained superabsorbent materials have a highly porous structure and can absorb a large amount of water molecules. Upon dehydration at room or body temperature while maintaining the three-dimensional network structures, the obtained superabsorbent materials can absorb a large amount of water, expand in volume and maintain a well-defined shape at room or body temperature, and under neutral or gastric conditions. Unlike the unprocessed water-soluble natural polysaccharides, which are easily degradable in stomach, the superabsorbent materials disclosed herein can maintain its three-dimensional network structure for a prolonged period even in the gastric environment at human body temperature. In other words, the superabsorbent materials disclosed herein requires higher than the gastric environment temperature (about 37° C.) to be re-dissolved in aqueous solution, thereby effectively overcoming the problem of quick metabolism and dissociation of water-soluble polysaccharides in gastric fluid when used as a weight-loss diet. The superabsorbent materials disclosed herein have superior swelling capacity and water retention properties under physiological conditions in gastric fluid, allowing them wide applications as dietary materials and/or delivery vehicles.

The superabsorbent materials disclosed herein have various applications in healthcare and food industries. For example, the superabsorbent material can be used as a medical diet or dietary supplement, which can increase the satiety of the patient thereby to reduce the intake of calories and carbohydrate. Such a diet or dietary supplement, when used in combination with a therapy, can enhance the therapeutic effect on obesity and diabetes; and even when used alone, can prevent or delay the onset of certain diseases such as obesity and diabetes. In some embodiments, the superabsorbent materials disclosed herein can be used as a vehicle for loading medicine for the preparation of medical materials.

One popular dietary strategy is volumetrics diet, which is the second best diet for weight loss and tied for the fifth best diet overall out of 40 diets evaluated by a panel of health experts in the 2018 U.S. News & World Report's Best Diet Rankings. The main concept of volumetrics diet is to eat natural foods that are low in calories and high in fiber or water such as fruits, vegetables, and soup. Although volumetrics diet has proven to be very effective in weight control and preventing obesity and diabetes, an apparent limitation of this strategy is the diversity of nutrients contained in each food that has high volume and water content but may lack certain essential nutrients. Nevertheless, two key features of volumetrics diet are low calorie density and high-water content. As used herein, the term "calorie density" means the total calories provided per mass unit measure of food. A diet having a low calorie density means that for the same mass or same weight, a low calorie density diet provides less calorie than a regular diet.

Some examples of the applications of the superabsorbent materials disclosed herein include but are not limited to the following: (1) the superabsorbent materials disclosed herein can be added to a cold or warm liquid diet or a drink such as water, juice, milk, beverage, soup, and pudding for human consumption; (2) the superabsorbent materials disclosed herein can be directly consumed in the form of a powder, a tablet, a capsule or any other suitable form, followed by drinking an appropriate amount of liquid to allow liquid absorption and swelling in the stomach; (3) the superabsorbent materials disclosed herein can be added as an ingredient to various food products such as bread, cakes, biscuits, energy bars and other foods to make low-calorie, dietary fiber-rich functional foods and/or volumetrics diet to induce satiety for a prolonged time. Because the superabsorbent materials disclosed herein can be in dry powder form and has superior swelling capacity, a small amount of consumption (about 5 g to 20 g) can achieve a satisfying satiety effect. The superabsorbent materials are also stable under normal shipping and storage conditions. Therefore, the superabsorbent materials can also be used as a vehicle to deliver drugs and other nutrients.

In some embodiments, the superabsorbent material or the dietary composition comprising the superabsorbent material further comprises one or more additional essential nutrients including macronutrients and micronutrients. Such nutrients include but are not limited to a variety of proteins and active peptides, vitamins and trace elements and minerals, and prebiotics.

In another aspect, disclosed herein is a method of preparing a superabsorbent material comprising agar, a combination of agar and one or more water-soluble natural polysaccharides. The method comprises the steps of: adding agar, a combination of agar and one or more water-soluble natural polysaccharide, to water to form a mixture, heating the mixture to a temperature of between 80° C. and 100° C. with stirring until the one or more polysaccharides are completely dissolved, allowing the mixture to cool down to between 20° C. and 45° C. to form a gel over a period of 2 to 10 hours (the temperature and time for the gelling step can be optimized depending on materials used), freezing the pre-formed gel at a temperature below freezing for at least 4 hours (the temperature and time for the cryogelation step can be optimized depending on materials used), and drying the frozen gel to obtain the superabsorbent material by thawing the gel and dry under normal pressure at 50-60° C. (referred to as thawing-dry), or dry the frozen gel by lyophilization (referred to as freeze-dry), or any drying methods that can remove water without damaging the gel matrix structure and diminishing the water absorption capacity and volume expansion function. In some embodiments, the method further comprises pulverizing the dried gel to obtain the superabsorbent material in a powder form of various mesh sized depending on specific application needs. In some embodiments, the drying step includes freeze-drying or vacuum freeze-drying the frozen gel. In some embodiments, the drying step includes thawing the frozen gel, filtering the thawed gel to obtain a filter cake, and drying the filter cake. The filter cake can be dried by any suitable method, including but not limited to air drying, heat drying, freeze-drying, vacuum drying, or a combination thereof.

The dried gel can be further pulverized into a powder form for easy storage and applications. As described herein, during the cooling process the agar, and one or more natural polysaccharides can form a three-dimensional structure. In some embodiments, a three-dimensional, porous structure is formed as shown by SEM images. After dehydration and swelling, the shape and form of this three-dimensional structure can be maintained. As demonstrated in the working examples, the swelled superabsorbent materials appeared in a non-flowing gel state with a well-defined shape. Thus, the superabsorbent materials obtained by the disclosed process have superior swelling capacity in terms of volume expansion and shape stability and water retention properties. Various water-soluble natural polysaccharides can be used, including but not limited to konjac gum, carrageenan, locust bean gum, xanthan gum, tamarind seed gum and guar gum carrageenan, alginate (such as sodium alginate), pectin, gellan gum, chitosan, Arabic gum, and a soluble starch.

As demonstrated in the working examples, different samples of the superabsorbent materials showed a wide range of water absorption capacity, suggesting that the composition, molar ratio and concentration can affect the properties of the superabsorbent materials. The disclosed superabsorbent materials are characterized by highly stable and uniform structure, suggesting that molecules of different natural polysaccharides interact with each other to form a new and unique matter, rather than simple physical mixtures of various polymers which would be expected to show heterogeneous structural features. The different composite natural polysaccharide materials made from different compositions, ratio and concentration clearly have different structures, which explain their different functionalities such as water absorption ratio and volume expansion ratio and shape stability. The liquid nitrogen flash freezing followed by lyophilization captured the porous structural features of various composite natural polysaccharides materials.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1: Materials and Methods

Preparation of artificial gastric juice (according to the United States Pharmacopoeia): 2.0 g sodium chloride, 3.2 g pepsin (1500 U/mg), and 7.0 ml of concentrated hydrochloric acid were added to distilled water and the volume was adjusted to 1000 ml.

Absorption ratio test: 1.0 g of a dry superabsorbent material was mixed with 250 g of distilled water in a beaker, and the mixture was allowed to stand for 3 hours at 25° C. Then the sample in the beaker was poured onto a 120-mesh sieve and kept for 1 hour at 25° C. to allow the water to drip off naturally. The wet sample remained on the sieve was recovered and weighed. The absorption ratio was calculated as follows:

Absorption ratio=the weight of the wet sample recovered from the sieve/the weight of the starting dry sample.

Similarly, the absorption ratio of a sample superabsorbent material in the artificial gastric juice was tested using the procedure described above. Instead of the distilled water, 1.0 g of the dry sample was mixed with the artificial gastric juice and allowed to stand for 3 hours at 37° C. Then the wet sample was recovered and weighed, and the absorption ratio was calculated as described above.

Gel strength test: 1.5 g of agar was added to 98.5 g of deionized water. The mixture was stirred and heated to 90° C. until the agar was completely dissolved, then cooled to 20° C. to form an agar gel. The gel was allowed to stand for 24 hours before use. 1.5 g of κ-carrageenan was added to 98.3 grams of deionized water. The mixture was stirred and heated to 90° C. until κ-carrageenan was completely dissolved. 0.2 g of potassium chloride was added and then cooled to 20° C. to form a carrageenan gel. The gel was allowed to stand for 24 hours before use. The prepared agar gel and the carrageenan gel were tested for gel strength using a texture analyzer (Stable Micro Systems, TA.XT. Plus Texture Analyser, UK). The test settings were: probe P/0.5, pressing speed 1.5 mm/s, running speed 1.0 mm/s, recovering speed 1.5 mm/s, and the pressing distance was 20 mm.

The agar gel and the carrageenan gel used herein had a measured gel strength of 1000 g/cm² and 1200 g/cm², respectively.

Viscosity test: 2.0 g of a water-soluble natural polysaccharide was added to 198 g of deionized water. The mixture was stirred at room temperature until the polysaccharide was completely dissolved. The viscosity of the solution was measured at 25° C. using a Brookfield viscometer. The measured viscosity of the starting materials used herein is listed in Table 1 below.

TABLE 1

| Viscosity of Starting Materials | |
| --- | --- |
| Polysaccharide | Viscosity |
| Konjac gum powder aqueous solution | 22000 mpa · s |
| Locust bean gum aqueous solution | 2500 mpa · s |
| Guar gum aqueous solution | 3500 mpa · s |
| Xanthan gum aqueous solution | 3200 mpa · s |
| Tamarind seed gum aqueous solution | 60 mpa · s |

Example 2

This example demonstrates the absorption ratio of a simple mixture of agar, κ-carrageenan, and konjac gum. Same amount of agar, κ-carrageenan, and konjac gum powder, 1 g of each, were mixed to form a simple mixture (Sample No. 1), and the absorption ratio of the simple mixture was measured using the method described in Example 1. Three sets of the experiment were conducted in parallel and the average of the measurements was taken. The mixture had a water absorption ratio of 4.0 and an artificial gastric juice absorption ratio of 2.6. The swelled sample formed in the absorption test appeared in a non-flowing gel state.

Example 3

This example demonstrates the absorption ratio of a superabsorbent material formed by agar, κ-carrageenan, and konjac gum. Same amount of agar, κ-carrageenan, and konjac gum powder, 1 g of each, were added to 197 g deionized water to form a mixture. The mixture was heated to 95° C. with stirring until the polysaccharides were completely dissolved, then slowly cooled to form a gel. The gel was kept at 10° C. for 2 hours, and then frozen for 10 hours in a −20° C. freezer to obtain a frozen gel. The frozen gel was subjected to freeze-drying to decrease the water content to 15-18% and pulverizing, thereby to obtain Sample No. 2. Alternatively, the frozen gel was thawed and filtered, and the filter cake was dried at 50° C. under the normal pressure to decrease the water content to 15-18% and then pulverized to obtain Sample No. 3. The absorption ratio of the samples was measured as described in Example 1. Three sets of the experiment were conducted in parallel and the average of the measurements was taken. Sample No. 2 had a water absorption ratio of 88.6 and an artificial gastric juice absorption ratio of 31.5. Sample No. 3 had a water absorption ratio of 97.2 and an artificial gastric juice absorption ratio of 34.5. Both swelled samples formed in the absorption test appeared in a non-flowing gel state.

Example 4

This example demonstrates the absorption ratio of a superabsorbent material formed by agar, κ-carrageenan, and konjac gum. 0.75 g agar, 0.75 g κ-carrageenan, and 1.5 g konjac gum powder were added to 197 g deionized water to form a mixture. The mixture was processed by the same method described in Example 3 to obtain Sample No. 4 (direct freeze drying) and Sample No. 5 (thawing and drying), respectively. Sample No. 4 had a water absorption ratio of 79.7 and an artificial gastric juice absorption ratio of 29.5. Sample No. 5 had a water absorption ratio of 95.3 and an artificial gastric juice absorption ratio of 34.1. Both swelled samples formed in the absorption test appeared in a non-flowing gel state.

Example 5

This example demonstrates the absorption ratio of a superabsorbent material formed by agar, κ-carrageenan, and konjac gum. 1.5 g agar, 0.75 g κ-carrageenan, and 0.75 g konjac gum powder were added to 197 g deionized water to form a mixture. The mixture was processed by the same method described in Example 3 to obtain Sample No. 6 (direct freeze drying) and Sample No. 7 (thawing and drying), respectively. Sample No. 6 had a water absorption ratio of 67.4 and an artificial gastric juice absorption ratio of 23.8. Sample No. 7 had a water absorption ratio of 68.9 and an artificial gastric juice absorption ratio of 26.0. Both swelled samples formed in the absorption test appeared in a non-flowing gel state.

Example 6

This example demonstrates the absorption ratio of a superabsorbent material formed by agar, κ-carrageenan, and konjac gum. 0.5 g agar, 1.0 g κ-carrageenan, and 0.5 g konjac gum powder were added to 198 g deionized water to form a mixture. The mixture was processed by the same method described in Example 3 to obtain Sample No. 8 (direct freeze drying) and Sample No. 9 (thawing and drying), respectively. Sample No. 8 had a water absorption ratio of 105.4 and an artificial gastric juice absorption ratio of 23.7. Sample No. 9 had a water absorption ratio of 121.0 and an artificial gastric juice absorption ratio of 27.6. Both swelled samples formed in the absorption test appeared in a non-flowing gel state.

Example 7

This example demonstrates the absorption ratio of a superabsorbent material formed by agar, κ-carrageenan, and konjac gum. 0.25 g agar, 0.5 g κ-carrageenan, and 0.25 g konjac gum powder were added to 199 g deionized water to form a mixture. The mixture was processed by the same method described in Example 3 to obtain Sample No. 10 (direct freeze drying) and Sample No. 11 (thawing and drying), respectively. Sample No. 10 had a water absorption ratio of 165.1 and an artificial gastric juice absorption ratio of 21.8. Sample No. 11 had a water absorption ratio of 195.0 and an artificial gastric juice absorption ratio of 26.5. Both swelled samples formed in the absorption test appeared in a non-flowing gel state.

Example 8

This example demonstrates the absorption ratio of a superabsorbent material formed by agar, κ-carrageenan, and konjac gum. 1.0 g agar, 2.0 g κ-carrageenan, and 1.0 g konjac gum powder were added to 196 g deionized water to form a mixture. The mixture was processed by the same method described in Example 3 to obtain Sample No. 12 (thawing and drying). Sample No. 12 had a water absorption ratio of 73.2 and an artificial gastric juice absorption ratio of 36.0. The swelled sample formed in the absorption test appeared in a non-flowing gel state.

Example 9

This example demonstrates the absorption ratio of a superabsorbent material formed by agar, κ-carrageenan, and konjac gum. 2.0 g agar, 4.0 g κ-carrageenan, and 2.0 g konjac gum powder were added to 192 g deionized water to form a mixture. The mixture was processed by the same method described in Example 3 to obtain Sample No. 13 (thawing and drying). Sample No. 13 had a water absorption ratio of 69.0 and an artificial gastric juice absorption ratio of 26.0. The swelled sample formed in the absorption test appeared in a non-flowing gel state.

Example 10

This example demonstrates the absorption ratio of a superabsorbent material formed by agar, κ-carrageenan, and locust bean gum. 1.5 g agar, 0.75 g κ-carrageenan, and 0.75 g locust bean gum powder were added to 197 g deionized water to form a mixture. The mixture was processed by the same method described in Example 3 to obtain Sample No. 14 (thawing and drying). Sample No. 14 had a water absorption ratio of 52.0 and an artificial gastric juice absorption ratio of 23.8. The swelled sample formed in the absorption test appeared in a non-flowing gel state.

Example 11

This example demonstrates the absorption ratio of a superabsorbent material formed by agar, κ-carrageenan, konjac gum, and xanthan gum. 1.0 g agar, 1.0 g κ-carrageenan, 0.4 g konjac gum powder, and 0.6 g xanthan gum powder were added to 197 g deionized water to form a mixture. The mixture was processed by the same method described in Example 3 to obtain Sample No. 15 (thawing and drying). Sample No. 15 had a water absorption ratio of 78.0 and an artificial gastric juice absorption ratio of 27.5. The swelled sample formed in the absorption test appeared in a non-flowing gel state.

Example 12

This example demonstrates the absorption ratio of a superabsorbent material formed by agar, κ-carrageenan, and tamarind seed gum. 0.8 g agar, 0.8 g κ-carrageenan, and 0.4 g tamarind seed gum powder were added to 198 g deionized water to form a mixture. The mixture was processed by the same method described in Example 3 to obtain Sample No. 16 (direct freeze drying). Sample No. 16 had a water absorption ratio of 48.0 and an artificial gastric juice absorption ratio of 20.5. The swelled sample formed in the absorption test appeared in a non-flowing gel state.

Example 13

This example demonstrates the absorption ratio of a superabsorbent material formed by agar, κ-carrageenan, and guar gum. 0.8 g agar, 0.8 g κ-carrageenan, and 0.4 g guar gum powder were added to 198 g deionized water to form a mixture. The mixture was processed by the same method described in Example 3 to obtain Sample No. 17 (direct freeze drying). Sample No. 17 had a water absorption ratio of 57.0 and an artificial gastric juice absorption ratio of 21.8. The swelled sample formed in the absorption test appeared in a non-flowing gel state.

Example 14

This example demonstrates the absorption ratio of a superabsorbent material formed by agar. 2.0 g agar was added to 198 g deionized water to form a mixture. The mixture was processed by the same method described in Example 3 to obtain Sample No. 18 (thawing and drying). Sample No. 18 had a water absorption ratio of 68.0 and an artificial gastric juice absorption ratio of 18.5. The swelled sample formed in the absorption test appeared in a non-flowing gel state.

Example 15

This example demonstrates the absorption ratio of a superabsorbent material formed by κ-carrageenan. 2.0 g κ-carrageenan was added to 198 g deionized water to form a mixture. The mixture was processed by the same method described in Example 3 to obtain Sample No. 19 (direct freeze drying). Sample No. 19 had a water absorption ratio of 32.7 and an artificial gastric juice absorption ratio of 15.6. The swelled sample formed in the absorption test appeared in a non-flowing gel state.

Example 16

This example demonstrates the absorption ratio of a superabsorbent material formed by agar, and konjac gum. 1.0 g agar, and 1.0 g konjac gum powder were added to 198 g deionized water to form a mixture. The mixture was processed by the same method described in Example 3 to obtain Sample No. 20 (thawing and drying). Sample No. 20 had a water absorption ratio of 36.0 and an artificial gastric juice absorption ratio of 20.5. The swelled sample formed in the absorption test appeared in a non-flowing gel state.

Example 17

This example demonstrates the absorption ratio of a superabsorbent material formed by κ-carrageenan, and konjac gum. 1.0 g κ-carrageenan, and 1.0 g konjac gum powder were added to 198 g deionized water to form a mixture. The mixture was processed by the same method described in Example 3 to obtain Sample No. 21 (direct freeze drying). Sample No. 21 had a water absorption ratio of 27.0 and an artificial gastric juice absorption ratio of 17.8. The swelled sample formed in the absorption test appeared in a non-flowing gel state.

The characteristics of all samples from Examples 2-17 are summarized in Table 2 below.

TABLE 2

Characterization of the Superabsorbent Materials

| Example No. | Sample No. | Ingredients and ratio | Preparation Condition | Absorption ratio in water | Absorption ratio in gastric juice |
|---|---|---|---|---|---|
| 2 | 1 | Agar:κ-carrageenan:konjac gum = 1:1:1 | Simple mixture | 4.0 | 2.6 |
| 3 | 2 | Agar:κ-carrageenan:konjac gum = 1:1:1 | Superabsorbent material obtained by direct freeze drying | 88.6 | 31.5 |
| 3 | 3 | Agar:κ-carrageenan:konjac gum = 1:1:1 | Superabsorbent material obtained by thawing and drying | 97.2 | 34.5 |
| 4 | 4 | Agar:κ-carrageenan:konjac gum = 1:1:2 | Superabsorbent material obtained by direct freeze drying | 79.7 | 29.5 |
| 4 | 5 | Agar:κ-carrageenan:konjac gum = 1:1:2 | Superabsorbent material obtained by thawing and drying | 95.3 | 34.1 |
| 5 | 6 | Agar:κ-carrageenan:konjac gum = 2:1:1 | Superabsorbent material obtained by direct freeze drying | 67.4 | 23.8 |
| 5 | 7 | Agar:κ-carrageenan:konjac gum = 2:1:1 | Superabsorbent material obtained by thawing and drying | 68.9 | 26.0 |
| 6 | 8 | Agar:κ-carrageenan:konjac gum = 1:2:1 | Superabsorbent material obtained by direct freeze drying | 105.4 | 23.7 |
| 6 | 9 | Agar:κ-carrageenan:konjac gum = 1:2:1 | Superabsorbent material obtained by thawing and drying | 121.0 | 27.6 |
| 7 | 10 | Agar:κ-carrageenan:konjac gum = 1:2:1 | Superabsorbent material obtained by direct freeze drying | 165.1 | 21.8 |
| 7 | 11 | Agar:κ-carrageenan:konjac gum = 1:2:1 | Superabsorbent material obtained by thawing and drying | 195.0 | 26.5 |
| 8 | 12 | Agar:κ-carrageenan:konjac gum = 1:2:1 | Superabsorbent material obtained by thawing and drying | 73.2 | 36.0 |
| 9 | 13 | Agar:κ-carrageenan:konjac gum = 1:2:1 | Superabsorbent material obtained by thawing and drying | 69.0 | 26.0 |
| 10 | 14 | Agar:κ-carrageenan:locust bean gum = 2:1:1 | Superabsorbent material obtained by thawing and drying | 52.0 | 23.8 |
| 11 | 15 | Agar:κ-carrageenan:konjac gum:xanthan gum = 5:5:2:3 | Superabsorbent material obtained by thawing and drying | 78.0 | 27.5 |
| 12 | 16 | Agar:κ-carrageenan : tamarind seed gum = 2:2:1 | Superabsorbent material obtained by direct freeze drying | 48.0 | 20.5 |
| 13 | 17 | Agar:κ-carrageenan:guar gum = 2:2:1 | Superabsorbent material obtained by direct freeze drying | 57.0 | 21.8 |
| 14 | 18 | Agar only | Superabsorbent material obtained by thawing and drying | 68.0 | 18.5 |
| 15 | 19 | κ-carrageenan only | Superabsorbent material obtained | 32.7 | 15.6 |

TABLE 2-continued

Characterization of the Superabsorbent Materials

| Example No. | Sample No. | Ingredients and ratio | Preparation Condition | Absorption ratio in water | Absorption ratio in gastric juice |
|---|---|---|---|---|---|
| 16 | 20 | Agar:konjac gum = 1:1 | Superabsorbent material obtained by direct freeze drying by thawing and drying | 36.0 | 20.5 |
| 17 | 21 | κ-carrageenan: konjac gum = 1:1 | Superabsorbent material obtained by direct freeze drying | 27.0 | 17.8 |

Example 18

This example demonstrates the preparation and characterization of additional samples of the superabsorbent materials, as shown in Table 3 below.

This batch of the samples were prepared by weighing each ingredient and add to deionized water at the ratio and mass concentration as indicated in Table 3, heating to 100° C. and stirring until all ingredients are fully dissolved. Each solution was cooled to 20° C. and stored in a 20° C.

TABLE 3

Characterization of Additional Samples of Superabsorbent Materials

| Sample No. | Ingredients and ratio | Concentration | Thawing/drying at 50-60° C. water absorption ratio (pH 7) | Thawing/drying at 50-60° C. water absorption ratio (pH 1) | Freeze-dry water absorption ratio (pH 7) | Freeze-dry water absorption ratio (pH 1) |
|---|---|---|---|---|---|---|
| 22 | agar | 1.20% | 11.9 | 9.2 | 30.2 | 22.4 |
| 23 | agar + konjac gum (1:1) | 0.6% + 0.6% | 18.4 | 19.3 | 43.7 | 41.0 |
| 24 | agar + konjac gum + carrageenan (10:1:1) | 1.0% + 0.1% + 0.1% | 13.1 | 12.0 | 33.2 | 27.9 |
| 25 | agar + konjac gum + carrageenan (2:1:1) | 0.6% + 0.3% + 0.3% | 31.3 | 21.5 | 56.9 | 37.8 |
| 26 | agar + konjac gum + carrageenan (1:1:1) | 0.4% + 0.4% + 0.4% | 58.8 | 36.1 | 66.9 | 48.8 |
| 27 | agar + konjac gum + carrageenan (2:5:5) | 0.2% + 0.5% + 0.5% | 67.6 | 46.4 | 89.2 | 58.8 |
| 28 | agar + konjac gum + xanthan gum (1:1:1) | 0.3% + 0.3% + 0.3% | 58.9 | 28.3 | n/a | n/a |
| 29 | agar + locust bean gum + carrageenan (1:1:1) | 0.4% + 0.4% + 0.4% | 34.2 | 24.0 | n/a | n/a |
| 30 | agar + locust bean gum + xanthan gum (1:1:1) | 0.3% + 0.3% + 0.3% | 44.9 | 20.3 | n/a | n/a |
| 31 | agar + konjac gum + xanthan gum (3:1:1) | 0.6% + 0.2% + 0.2% | 37.7 | 18.7 | n/a | n/a |
| 32 | agar + locust bean gum + carrageenan (3:1:1) | 0.6% + 0.2% + 0.2% | 20.3 | 16.1 | n/a | n/a | incubator for 6 hours, to form a stable gel. After 6 hours, the samples were transferred to a −20° C. freezer to store for 10 hours, thereby to obtain cryo-stabilized gel. After 10 hours, the cryo-stabilized gel was thawed at room temperature, excess water was filtered off, and the sample was further air dried in a 50° C. incubator. Alternatively, after 10 hours of cryogelation at −20° C., the sample was lyophilized to dry where the gel was pre-frozen until its center reached −40° C., and the sample was kept below −10° C. throughout the lyophilization process until the sample was dry. The dried sample was pulverized to 20 mesh to obtain the powdered superabsorbent materials. The absorption ratio at different pH conditions was measured as described above.

As shown in Table 3, freeze-dry generally led to a higher water absorption ratio than thawing dry. Since drying process was after the gel formation (20° C. for 6 hours) and stabilization by cryogelation (−20° C. for 10 hours), it is unlikely that the freezing methods will produce different structures. However, during thawing dry process, it is likely that the water was melted and some of the pores were collapsed. While most of the pore can be reformed upon rehydration, a fraction of pores may not be re-established, presumably because some of the surfaces that form the wall of the pore become associated with each other so strongly that they cannot be separated upon rehydration. By contrast, during freeze dry process, the water remained in its solid form and removed by sublimation, so the pore structure may be better maintained. The types of materials also contributed to different properties of the superabsorbent materials. As shown in Table 3, Sample Nos. 22-25 demonstrated significantly different properties in the samples prepared by two different drying methods, suggesting their pore structures are more sensitive to the drying methods, whereas Sample Nos. 26 and 27 are less sensitive.

Example 19

This example demonstrates the volume expansion and shape stability of Sample Nos. 22-32.

Sample Nos. 22-32 were soaked in deionized water for 24 hours, and images of a particle of each sample were taken before and after rehydration using a Leica light microscope (model MZ125), as shown in FIG. 1.

Sample No. 22 showed low volume expansion but had a well-defined shape. Sample No. 23 showed low to modest volume expansion and had a well-defined shape. Sample No. 24 showed a sheet-like expansion, appeared to be an inter-connected bundle of fibers but did not have a well-defined gel matrix shape. Sample No. 25 showed low-to-modest volume expansion and the shape appeared to be stacked sheets. Sample No. 26 showed high volume expansion but appeared to have an inter-connected, heterogeneous sheet structures. Sample No. 27 showed large volume expansion. After fully swollen, Sample No. 27 had a well-defined shape that appeared to have a homogeneous gel matrix structure. Sample No. 28 showed high volume expansion but appeared to have an inter-connected, heterogeneous sheet structures. Sample No. 29 showed good volume expansion and good shape structure as a well-defined homogeneous gel matrix structure. Sample Nos. 30 and 31 were similar to Sample No. 29 and showed good volume expansion and good shape structure as a well-defined homogeneous gel matrix structure. Sample No. 32 was similar to Sample No. 24 and showed a sheet-like expansion, appeared to be an inter-connected bundle of fibers but did not have a well-defined gel matrix shape.

Thus, various samples expanded in volume upon rehydration, and the degree of volume expansion generally correlated with the water absorption ratio measured by weight. However, not all samples had a well-defined shape upon rehydration. For examples, Sample Nos. 24, 28, and 33, and to a lesser degree also Sample No. 26, had a looser structure in the rehydrated form. By contrast, Sample No. 27 had the best maintained shape.

Example 20

This example demonstrates the water absorption ratio and volume expansion kinetics of Sample No. 27.

Figure 2:
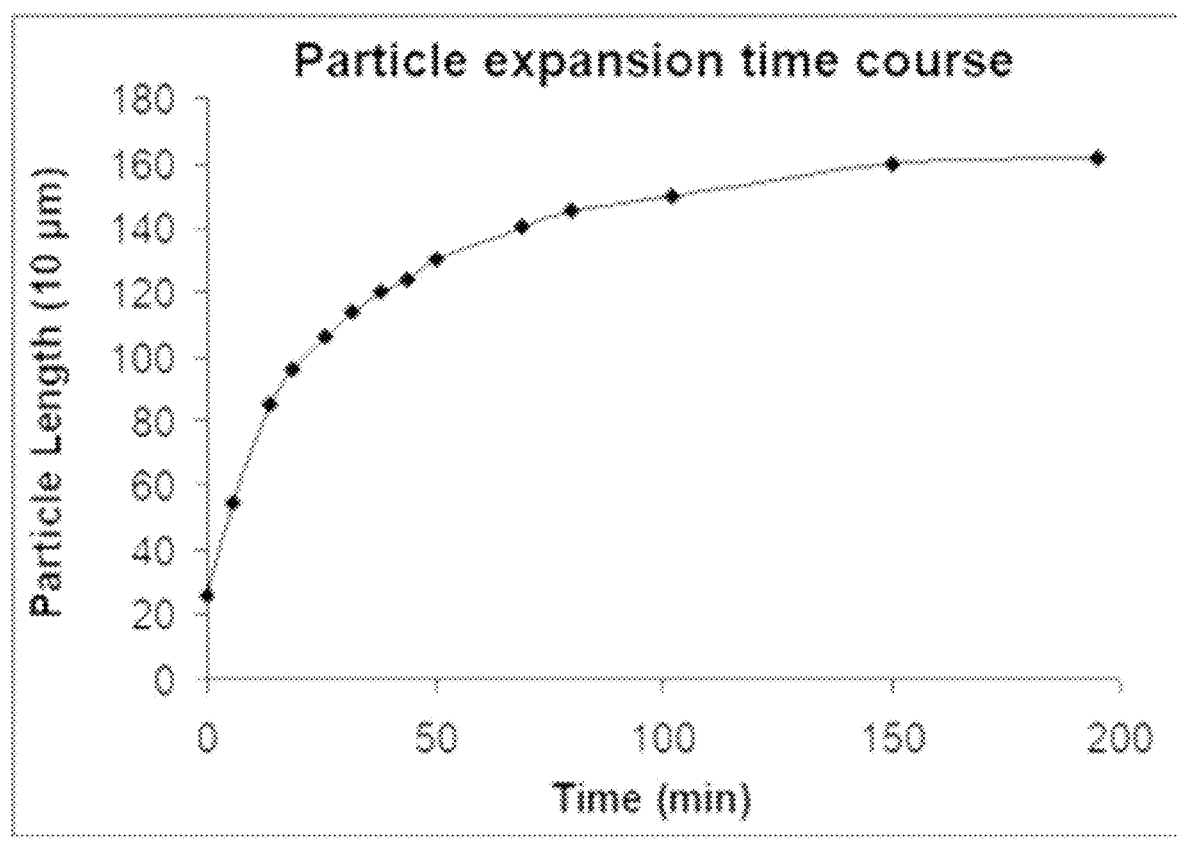
FIG. 2 shows the kinetics of water absorption and volume expansion of Sample No. 27.

Kinetic analysis of water absorption and volume expansion was performed on Sample No. 27. A dry particle of Sample No. 27 was swelled in deionized water (pH7) and FIG. 2 shows the length of the particle at various time points. The kinetic analysis showed that the sample particle underwent volume expansion rapidly upon rehydration, more than doubling its size in less than 6 minutes, expanding volume by 16-fold in 19 minutes, and eventually reaching a volume that was approximately 120-fold of the original volume of the dry particle. Most of the expansion was completed within 100 minutes (reaching 90% of the maximally expanded volume).

Example 21

This example demonstrates the scanning electron microscopic imaging (SEM) analysis of various samples.

Figure 3:
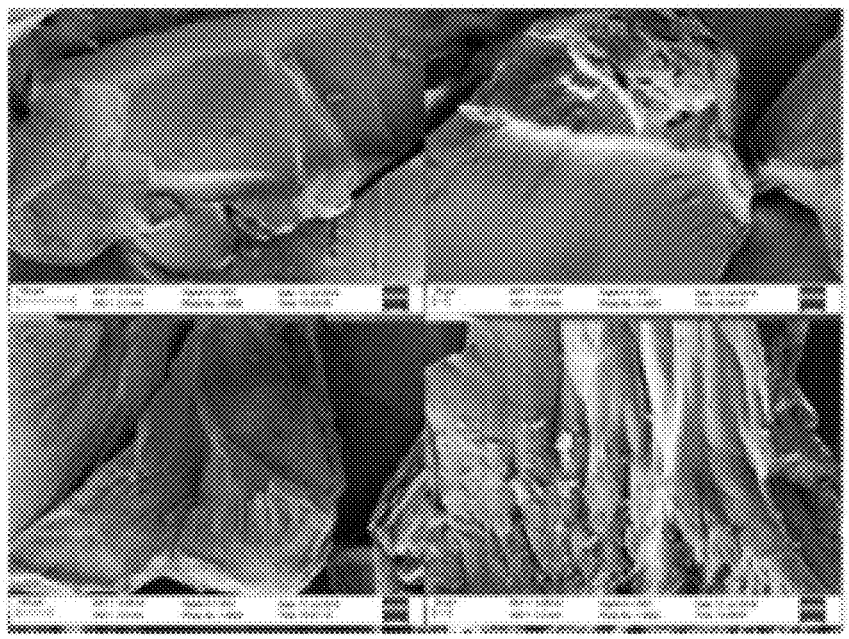
FIG. 3 shows the SEM images of the dry state of Sample Nos. 22, 23, 24 and 27 from thawing dry process.
Figure 3:
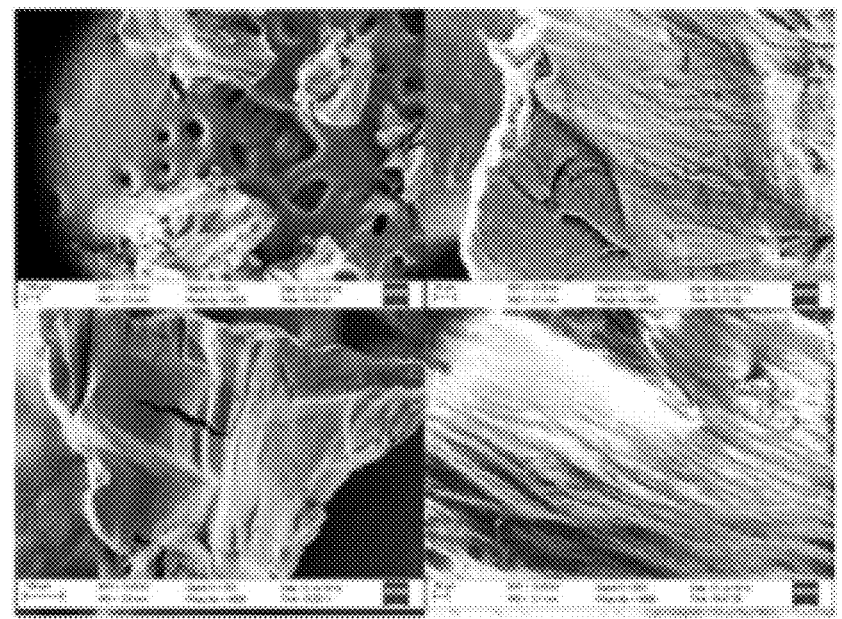

Sample Nos. 22-32 from thawing-dry preparation were Sputter coater coated with Pt and imaged on a JOEL JSM-7001 Scanning electron microscope. FIG. 3 shows the SEM images for Sample Nos, 22, 23, 24, and 27 from thawing dry.

Although different samples showed various surface features, it was hard to determine if such features were intrinsic to a given composite nature polysaccharide material, because the particle surface may be affected by the pulverization processes. FIG. 3 shows the SEM images of Sample Nos, 22, 23, 24, and 27 from thawing dry, each with two different magnifications and perspectives. Sample No. 27, and to a lesser degree also Sample No. 24, showed some parallelly organized surface structure as compared to the other two samples. However, the correlation to the functionalities such as water absorption and volume expansion of this observation is unclear. In general, the samples prepared by thawing-dry did not show any porous structures. However, by water absorption ratio measurement and volume expansion, these samples showed substantial ability to absorb water and expand in volume upon rehydration, suggesting that the matrix structure of the composite polysaccharide material is largely preserved in the thawing-dry process and can be fully or substantially established upon rehydration.

Example 22

This example demonstrates the scanning electron microscopic imaging (SEM) analysis of hydrated samples prepared by flash freezing and freeze-drying at different pH conditions: at pH 7 and at pH 1, respectively.

To capture the structural features in the hydrated state, thawing-dried samples from Table 3 were soaked in deionized water (pH=7 or pH=1) for at least 12 hours, flash frozen in liquid nitrogen, and lyophilized to dry, sputter coated with platinum and imaged on a JOEL JSM-7001 Scanning electron microscope. For each sample, a number of particles were imaged, images most representative of the observed structural features of a given sample are shown. For each sample, two different perspectives are shown in FIG. 4 (pH 7) and FIG. 5 (pH 1), respectively.

Figure 4:
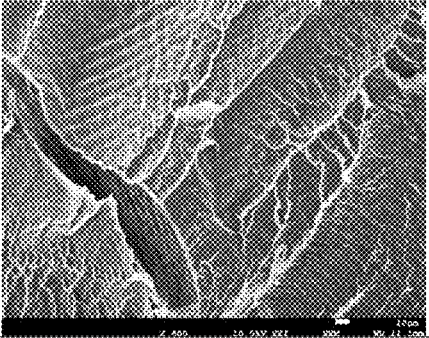
FIG. 4 shows the SEM images of hydrated thawing-dried Sample Nos. 22-32 prepared by liquid nitrogen flash freezing (pH=7).
Figure 4:
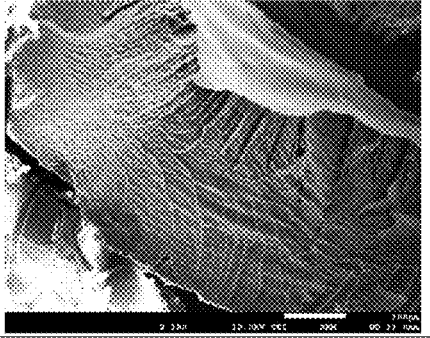
Figure 4:
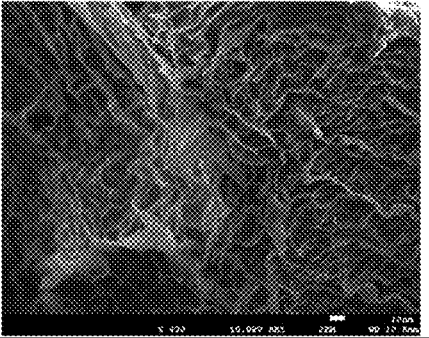
Figure 4:
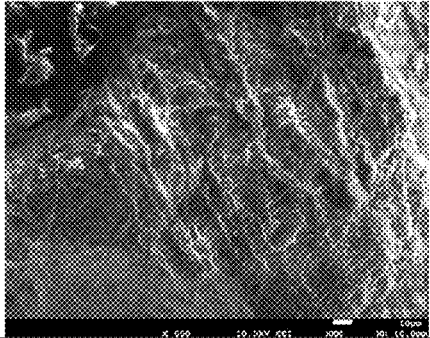
Figure 4:
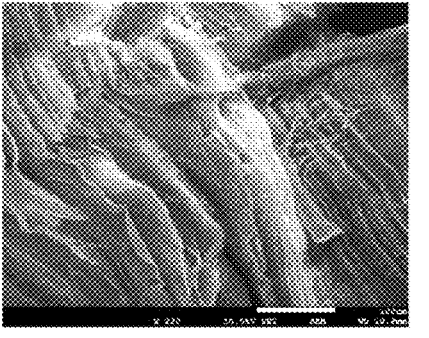
Figure 4:
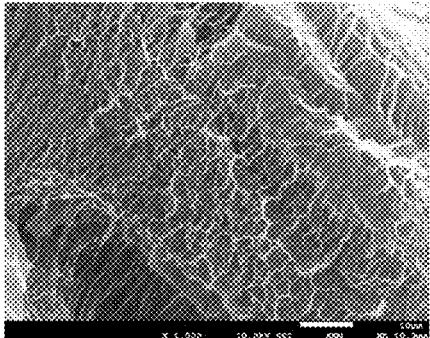
Figure 4:
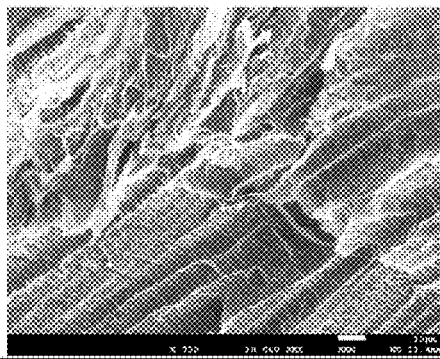
Figure 4:
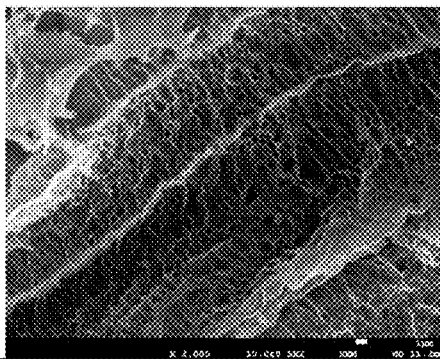
Figure 4:
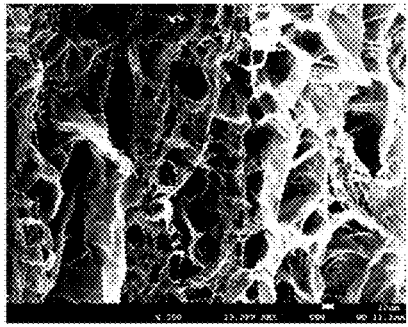
Figure 4:
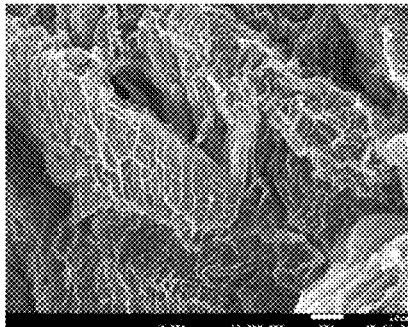
Figure 4:
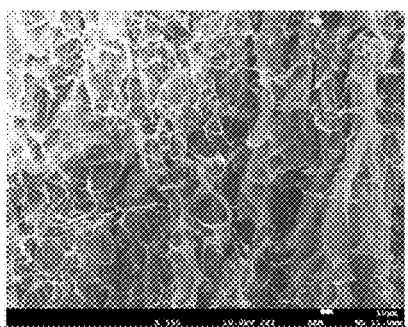
Figure 4:
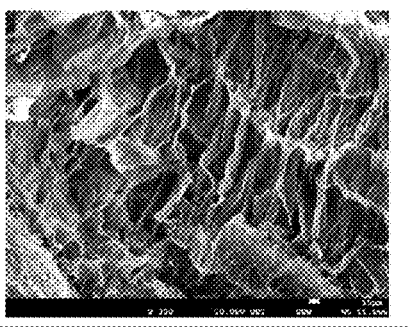
Figure 4:
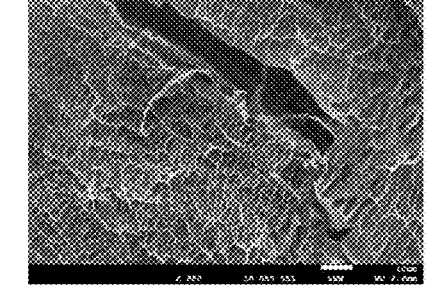
Figure 4:
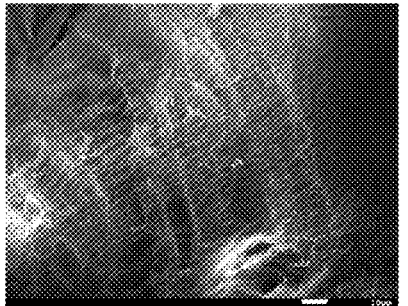
Figure 4:
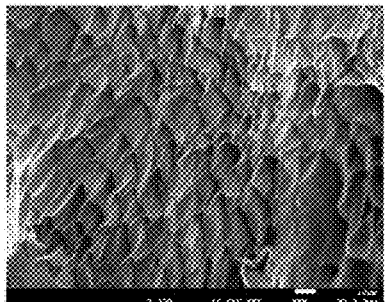
Figure 4:
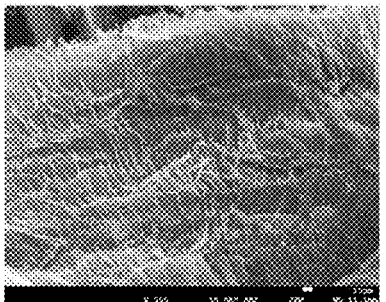
Figure 4:
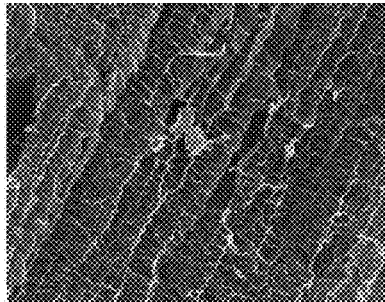
Figure 4:
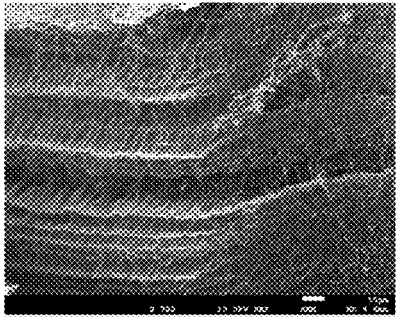
Figure 4:
Figure 4:
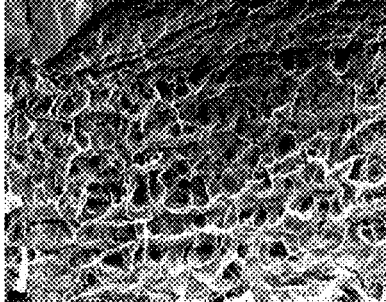
Figure 4:
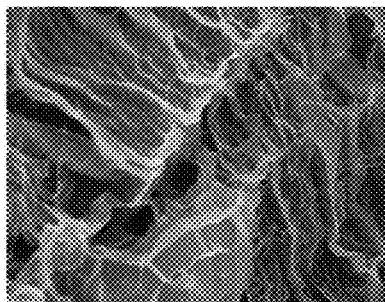
Figure 4:

As shown in FIG. 4, at pH 7, Sample No. 22 had a relatively dense structure, the picture on the right showed some layered structural feature at the surface, which could be responsible for a certain level of water absorption observed with this sample. Sample No. 23 showed a cross-layered pore structure on one face (left) and a fibrous pore structure on the other face (right). Although the right picture gives a puffy appearance, the pore size seemed to be very small. Sample No. 24 showed a parallel-layered structure (left). The zoom-in view on the right showed that each layer contains a network of small pores (right). Sample No. 25 showed a parallel-layered structure (left). The zoom-in view on the right shows that each layer contained a network of pores that were approximately 1-5 μm wide, and 5-10 μm long (right), these pores were interconnected and intertwined with each other. Sample No. 26 showed a very porous structure but the pore structural pattern was less well-defined (left). Its surface did show a pattern of cross-layered pore (right). Sample No. 27 showed a characteristic parallel-layered large pore (10-20 μm wide, and 100-200 μm long) that seemed to be very deep (right). In another cross-section view (left), the parallel-layered large pore seemed to be connected by many thin fibers. Sample No. 28 had a very porous structure that showed cross-layered pore pattern on one face (left) and a puffy loose parallel fiber structure on the other (right). Sample No. 29 had a porous structure that resembled the pattern of fish scale on one face (left) and layered sheets on the other (right). Sample No. 30 had a porous structure that seemed to be intertwined on one face (left) and parallelly aligned on the other (right). Sample No. 31 had the structural features of parallel layers (left) and honeycomb-like pore (right). Sample No. 32 had a loose layered structural feature on one face (left) and a more densely packed layer structure on the other face (right).

Figure 5:
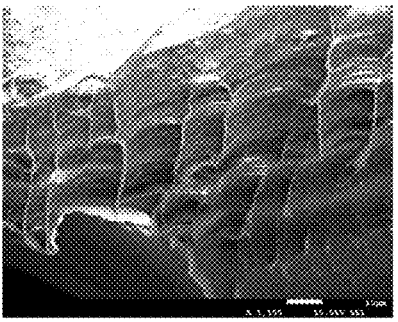
FIG. 5 shows the SEM images of hydrated thawing-dried samples Nos. 22-27, 31, and 32 prepared by liquid nitrogen flash freezing (pH=1).
Figure 5:
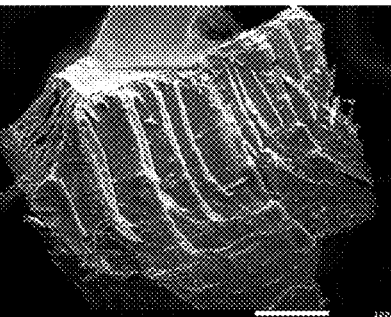
Figure 5:
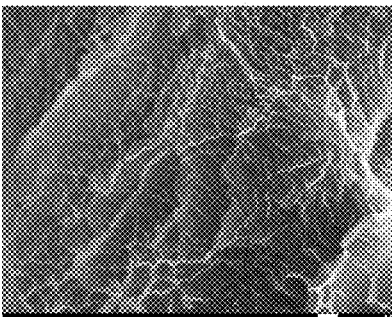
Figure 5:
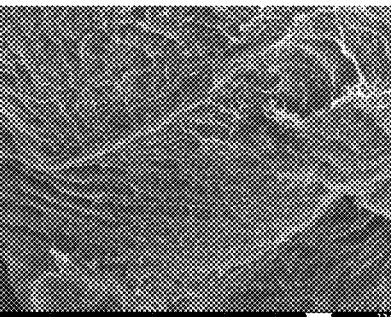
Figure 5:
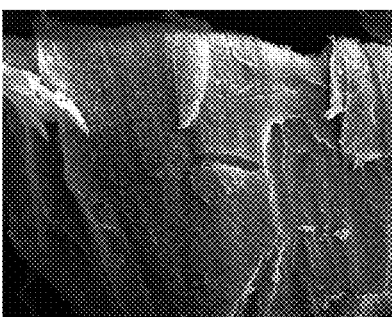
Figure 5:
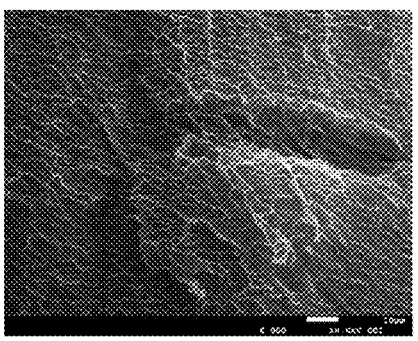
Figure 5:
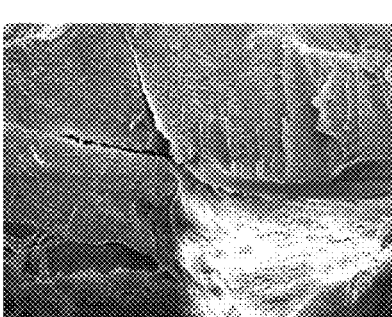
Figure 5:
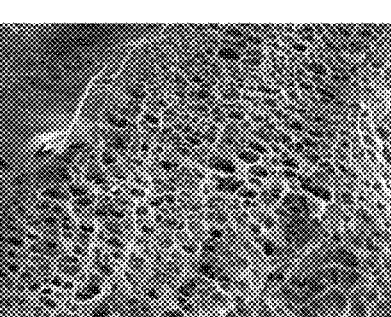
Figure 5:
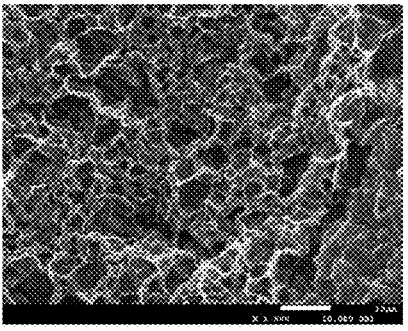
Figure 5:
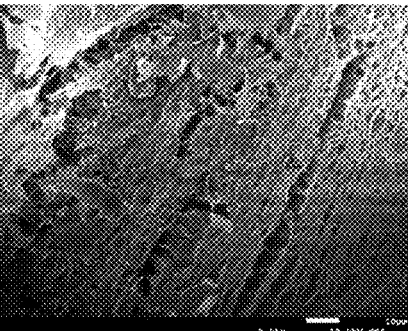
Figure 5:
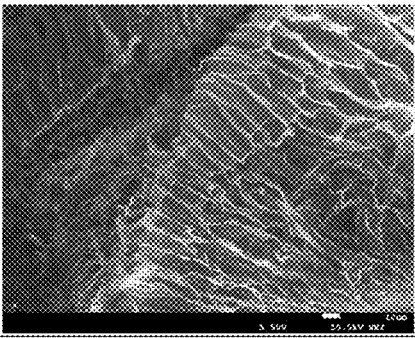
Figure 5:
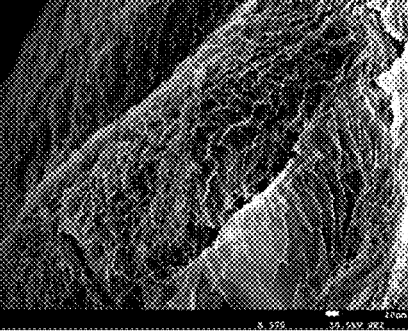
Figure 5:
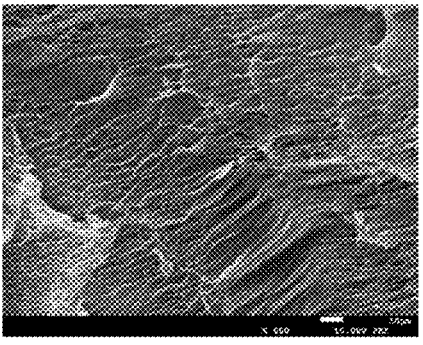
Figure 5:
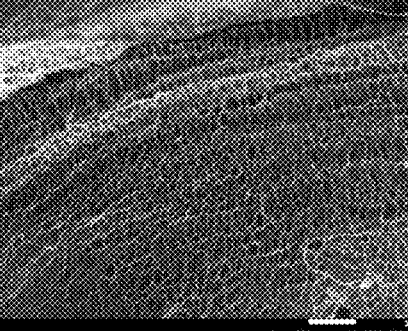
Figure 5:
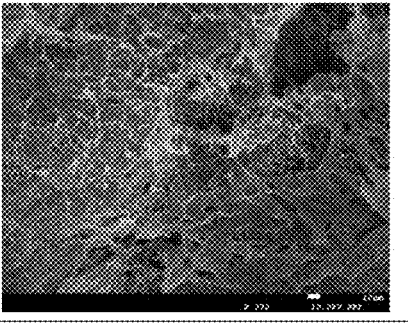
Figure 5:
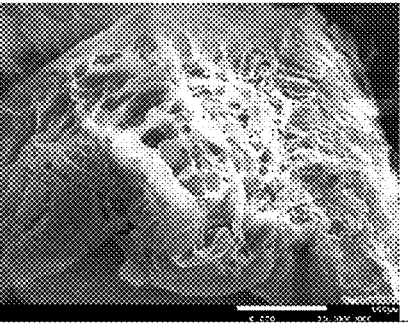

As shown in FIG. 5, the structural features of samples hydrated in pH 1 solution were generally similar to those observed with samples hydrated in pH 7 solution, although the pore size seemed to be smaller (for example, comparing pore size of Sample No. 25 at pH 7 and pH 1). FIG. 5 shows Sample Nos. 22-27, 31, and 32. Other samples not shown in FIG. 5 were also similar to their pH 7 counterpart in structures. These analyses strongly that the structural features observed were stable under different conditions and that the highly reproducible structural features were likely intrinsic property of each composite natural polysaccharide.

Example 23

This example demonstrates the scanning electron microscopic imaging (SEM) analysis of hydrated samples prepared by freeze drying. The samples were prepared by freeze drying (see the last two columns of Table 3). Briefly, the samples were prepared by weighing each ingredient and adding to deionized water at the ratio and mass concentration as indicated in Table 3, heating to 100° C. and stirring until all ingredients are fully dissolved. Each solution was cooled to 20° C. and stored in a 20° C. incubator for 6 hours, to form a stable gel. After 6 hours, the samples were transferred to a −20° C. freezer to store for 10 hours, thereby to obtain a cryo-stabilized gel. After 10 hours, the cryo-stabilized gel was pre-frozen until its center reached −40° C. and subjected to lyophilization. The sample was kept below −10° C. throughout the lyophilization process until the sample was dry.

Figure 6:
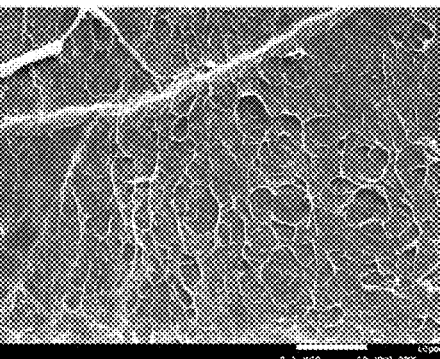
FIG. 6 shows the SEM images of hydrated freeze-dried samples Nos. 22-27 prepared by liquid nitrogen flash freezing (pH=7).
Figure 6:
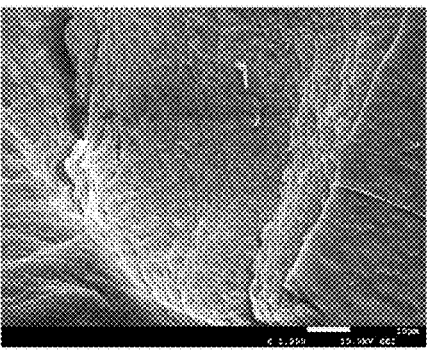
Figure 6:
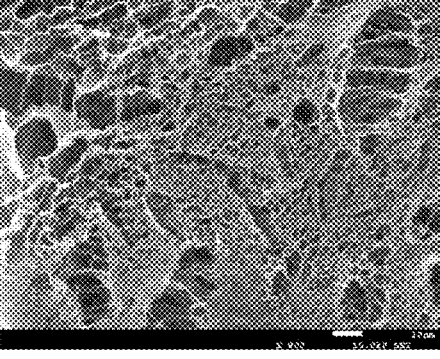
Figure 6:
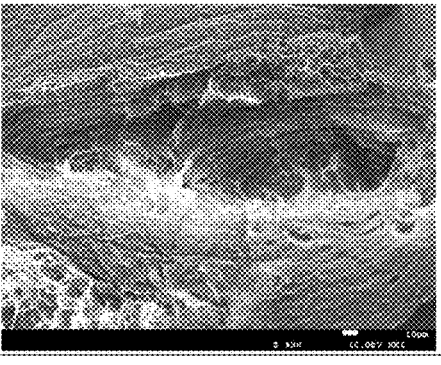
Figure 6:
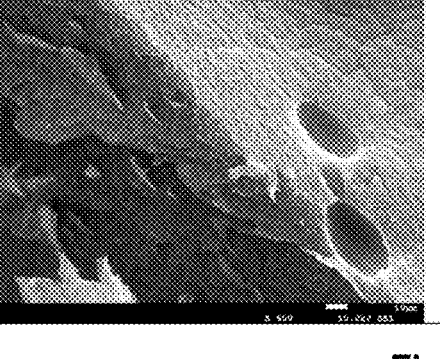
Figure 6:
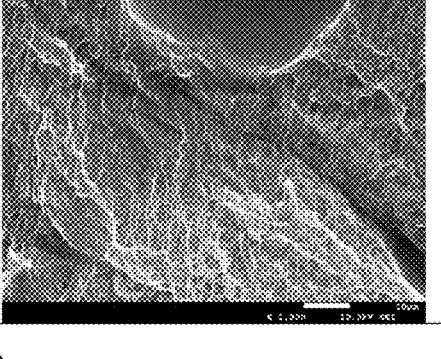
Figure 6:
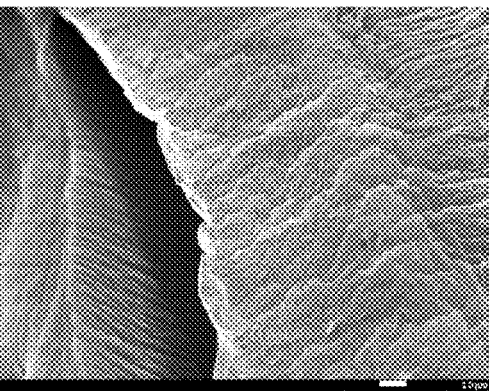
Figure 6:
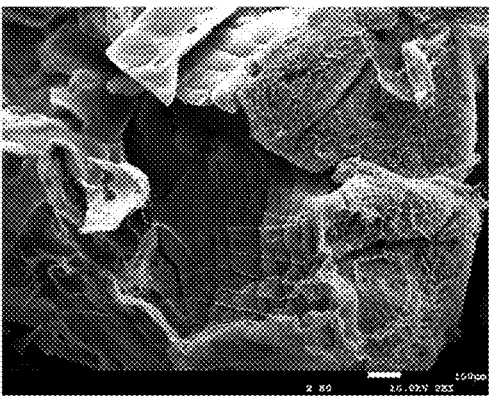
Figure 6:
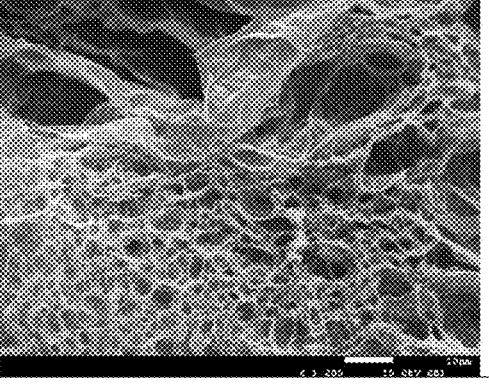
Figure 6:
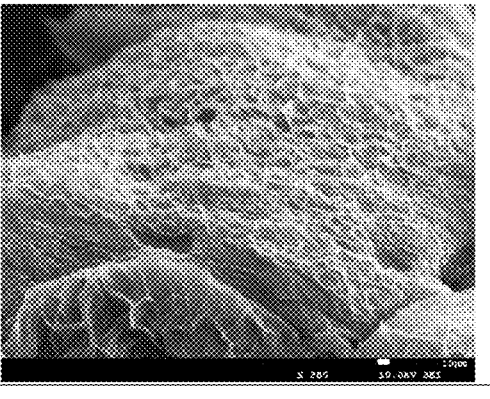
Figure 6:
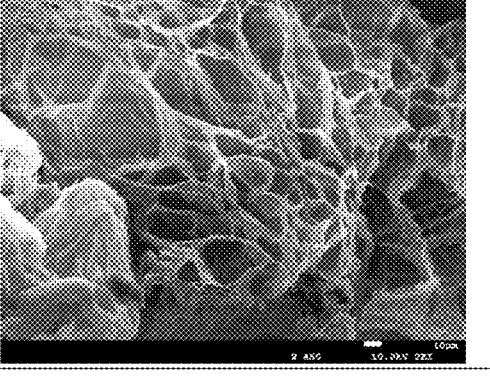
Figure 6:
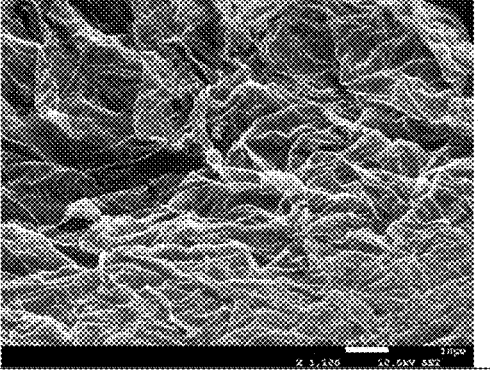

To capture the structural features in the hydrated state of freeze-dried samples from Table 3 (last two columns), sample particles were soaked in deionized water (pH=7) for more than 12 hours, flash frozen in liquid nitrogen, and lyophilized to dry, sputter coated with platinum and imaged on a JOEL JSM-7001 Scanning electron microscope. For each sample, a number of particles were imaged, images most representative of the observed structural features of a given sample are shown. For each sample, two different perspectives are shown in FIG. 6.

Sample No. 22 from freeze drying had a relatively dense structure, the picture on the right showed some layered structural feature at the surface, which could be responsible for a certain level of water absorption observed with this sample. Sample No. 23 from freeze drying showed a cross-layered pore structure at upper left corner of the figure on the left; when viewed at the cross-section (center of the left figure) the interconnected pore structure was apparent. The picture on the right shows fibrous pore structure from a different perspective (right). Sample 24 from freeze-drying showed a fine parallel-layered structure on the surface (left). The cut cross-section on the right shows that each layer contained a network of pores (right). Sample 25 from freeze drying showed a parallel-layered structure on the surface (left). The zoom-in view on the right shows that each layer contained a network of pores that were approximately 1-5 μm wide, and 5-10 μm long (right), these pores were interconnected and intertwined with each other. Sample No. 26 from freeze drying showed a very porous structure, but the pore structural pattern was less well-defined (left). Its surface did show a pattern of cross-layered pore (right). Sample No. 27 from freeze drying showed a characteristic interconnected pore pattern (left). The parallel-layered was also apparent on the surface (right).

Overall, the structural features and pore pattern of freeze-dried samples in this example were similar to those observed for corresponding samples prepared by thawing-drying, although the pore sizes and the overall dry volume of the samples prepared by freeze drying were larger than their counterparts prepared by thawing drying, especially for Sample Nos. 22-25.

The invention claimed is:

1. A method of preparing a superabsorbent material that comprises two or more water-soluble natural polysaccharides, comprising:
 Combining the two or more water-soluble natural polysaccharides with water to form a mixture;
 heating the mixture until the two or more polysaccharides are completely dissolved;
 cooling the mixture to form a gel;
 freezing the gel to obtain a frozen gel;
 thawing the frozen gel to obtain a thawed gel; and
 drying the thawed gel at a temperature of between 50° C. and 60° C. to obtain the superabsorbent material;
 wherein the superabsorbent material has a volume expansion ratio of at least 5 in deionized water at 25° C.

2. The method of claim 1, wherein the heating of the mixture is performed at a temperature of between 80° C. and 100° C.

3. The method of claim 1, further comprising pulverizing the superabsorbent material to obtain the superabsorbent material in a powder form.

4. A method of preparing a superabsorbent material that comprises two or more water-soluble natural polysaccharides, comprising:
- combining the two or more water-soluble natural polysaccharides with water to form a mixture;
- heating the mixture until the two or more polysaccharides are completely dissolved;
- cooling the mixture to form a gel;
- freezing the gel to obtain a frozen gel;
- thawing the frozen gel to obtain a thawed gel;
- filtering the thawed gel to obtain a filter cake gel; and
- drying the filter cake gel to obtain the superabsorbent material;
- wherein the superabsorbent material has a volume expansion ratio of at least 5 in deionized water at 25° C.

5. The method of claim 4, wherein the filter cake gel is dried by air drying, heat drying, freeze-drying, vacuum drying, or a combination thereof.

6. The method of claim 1, wherein the two or more water-soluble natural polysaccharides are selected from the group consisting of agar, konjac gum, carrageenan, locust bean gum, xanthan gum, tamarind seed gum and guar gum carrageenan, alginate, pectin, gellan gum, chitosan, Arabic gum, a soluble starch, and a combination thereof.

7. The method of claim 1, wherein the two or more water-soluble natural polysaccharides form a porous structure without any chemical cross-linking.

8. The method of claim 1, wherein the superabsorbent material is capable of expanding in volume in less than 2 hours, and maintaining a well-defined shape for at least 24 hours, under a neutral pH condition or a human gastric pH condition, and at room temperature or at human body temperature.

9. The method of claim 1, wherein the superabsorbent material has an absorption ratio of at least 10 or up to 200 in deionized water at 25° C.

10. The method of claim 1, wherein the superabsorbent material has a volume expansion ratio of at least 5 or up to 100 in artificial gastric juice at 37° C.

11. The method of claim 1, further comprising formulating the superabsorbent material into a dietary composition.

12. The method of claim 1, wherein the superabsorbent material has an absorption ratio of at least 5 or up to 100 in artificial gastric juice at 37° C.

13. The method of claim 1, wherein the superabsorbent material comprises agar and one or more water-soluble natural polysaccharides.

14. A method of preparing a superabsorbent material that comprises agar, carrageenan, and konjac gum, comprising:
- combining agar, carrageenan, and konjac gum with water to form a mixture;
- heating the mixture until the agar, carrageenan, and konjac gum are completely dissolved;
- cooling the mixture to form a gel;
- freezing the gel to obtain a frozen gel;
- thawing the frozen gel to obtain a thawed gel; and
- drying the thawed gel to obtain the superabsorbent material;
- wherein the superabsorbent material has a volume expansion ratio of at least 5 in deionized water at 25° C.; and
- wherein the superabsorbent material comprises at least 10% by weight of agar or at least 20% by weight of carrageenan; or wherein the superabsorbent material comprises agar, carrageenan, and konjac gum at a weight ratio of 10:1:1, 1:1:1, 1:1:2, 1:2:1, 2:1:1, or 2:5:5.

15. The method of claim 14, wherein the superabsorbent material comprises at least 10% by weight of agar.

16. The method of claim 14, wherein the superabsorbent material comprises at least 20% by weight of carrageenan.

17. The method of claim 14, wherein the superabsorbent material comprises agar, carrageenan, and konjac gum at a weight ratio of 10:1:1, 1:1:1, 1:1:2, 1:2:1, 2:1:1, or 2:5:5.

18. The method of claim 14, wherein the superabsorbent material comprises agar, carrageenan, and konjac gum at a weight ratio of 1:1:1, 1:1:2, or 1:2:1.

19. The method of claim 1, wherein the superabsorbent material has an absorption ratio of at least 20 and up to 200 in deionized water at 25° C.

20. The method of claim 1, wherein the superabsorbent material has an absorption ratio of at least 50 and up to 200 in deionized water at 25° C.

21. The method of claim 1, wherein the superabsorbent material has an absorption ratio of at least 100 and up to 200 in deionized water at 25° C.

* * * * *